US008133465B2

(12) United States Patent
Dai et al.

(10) Patent No.: US 8,133,465 B2
(45) Date of Patent: Mar. 13, 2012

(54) POLYMER-CARBON NANOTUBE COMPOSITE FOR USE AS A SENSOR

(75) Inventors: Liming Dai, Beavercreek, OH (US); Wei Chen, New York, NY (US)

(73) Assignee: University of Dayton, Dayton, OH (US)

( * ) Notice: Subject to any disclaimer, the term of this patent is extended or adjusted under 35 U.S.C. 154(b) by 1553 days.

(21) Appl. No.: 11/518,832

(22) Filed: Sep. 11, 2006

(65) Prior Publication Data

US 2012/0037306 A1 Feb. 16, 2012

Related U.S. Application Data

(60) Provisional application No. 60/716,112, filed on Sep. 12, 2005.

(51) Int. Cl.
*H01L 21/00* (2006.01)
(52) U.S. Cl. ........... 423/445 R; 423/445 B; 252/502; 252/510; 252/511; 438/22; 310/319; 977/707; 977/742; 977/783; 977/842; 977/953; 977/932
(58) Field of Classification Search .......... 252/500–511; 423/445 R, 445 B; 977/707, 742, 783, 842, 977/932, 953; 438/22; 310/319
See application file for complete search history.

(56) References Cited

U.S. PATENT DOCUMENTS

| 2002/0046872 | A1* | 4/2002 | Smalley et al. | 174/137 A |
| 2005/0287064 | A1* | 12/2005 | Mayne et al. | 423/445 B |
| 2006/0166810 | A1* | 7/2006 | Gunderman et al. | 502/64 |
| 2007/0138010 | A1* | 6/2007 | Ajayan | 204/400 |
| 2007/0189953 | A1* | 8/2007 | Bai et al. | 423/414 |
| 2007/0265379 | A1* | 11/2007 | Chen et al. | 524/404 |

FOREIGN PATENT DOCUMENTS

| CN | 1433962 A | | 8/2003 |
| WO | WO 02/16257 A2 | | 2/2002 |
| WO | WO2005/075341 | * | 8/2005 |

OTHER PUBLICATIONS

Raravikar et al. (Synthesis and characterization of thickness-aligned carbon-polymer composite films. Chem Mater., 17, pp. 974-983, web pub. Jan. 22, 2005).*

Li, J. et al., "A Gas Sensor Array Using Carbon Nanotubes and Microfabrication Technology" Electrochemical and Solid-State Letters 2005, 8, H100-H102.

Hughes et al "Electrochemical Capacitance of Nanocomposite Films Formed by Coating Aligned Arrays of Carbon Nanotubes with Polypyrrole" Advanced Materials, vol. 14, No. 5, Mar. 4, 2002, pp. 382-385.

(Continued)

*Primary Examiner* — Mark Kopec
*Assistant Examiner* — Tri V Nguyen
(74) *Attorney, Agent, or Firm* — Dinsmore & Shohl LLP

(57) ABSTRACT

A polymer-carbon nanotube composite film is provided for use as a sensor for detecting chemical vapors. The composite film is formed by coating perpendicularly-aligned carbon nanotubes with a polymer selected from poly(vinyl acetate), poly(isoprene), or blends thereof. The sensor may be formed by attaching at least two electrodes to the polymer-carbon nanotube composite film. The sensor may be used in any applications where the sensor is capable of detecting a change in conductivity in the composite.

7 Claims, 3 Drawing Sheets

OTHER PUBLICATIONS

Feng et al "Well-aligned polyaniline/carbon-nanotube composite films grown by in-situ aniline polymerization" Carbon, vol. 41, No. 8, 2003, pp. 1551-1557.

Santhanam et al "A chemical sensor for chloromethanes using a nanocomposite of multiwalled carbon nanotubes with poly(3-methylthiophene)" Sensors and Actuators B, vol. 106, No. 2, May 13, 2005, pp. 766-771.

Wenchao et al. "Ultraviolet irradiated trans-polyisoprene/carbon nanotubes composite" China Synthetic Rubber Industry, 2003, 26(6), pp. 365-367.

Chinese Office Action dated May 27, 2010 pertaining to Chinese Application for Invention No. 200680037185.7.

Chen, Shi Guo et al., "Effects of temperature and vapor pressure on the gas sensing behavior of carbon black filled polyurethane composites", Elsevier, Sensors and Actuators B 105 (2005). pp. 187-193.

Koul, Sarswati et al., "Conducting polyaniline composite: a reusable sensor material for aqueous ammonia", Elsevier, Sensors and Actuators B 75 (2001), pp. 151-159.

Kong, Jing et al., Article: Nanotube Molecular Wires as Chemical Sensors, http://web.ebscohost.com, Dec. 19, 2006, pp. 1-6.

Collins, Philip G. et al., Article: "Extreme Oxygen Sensitivity of Electronic Properties of Carbon Nanotubes", http:/web.ebscohost.com, Dec. 19, 2006, pp. 1-8.

Snow, E.S. et al., "Chemical Detection with a Single-Walled Carbon Nanotube Capacitor", Science 307, 1942-1945 (2005).

Yang, Yongyuan et al., "Patterned Growth of Well-Aligned Carbon Nanotubes: A Photolithographic Approach," J. Am. Chem. Soc. 1999, 121, pp. 10832-10833.

He, Pingang et al., "Aligned carbon nanotube-DNA electrochemical sensors", Chem. Commun., 2004, pp. 348-349.

Dai, Liming et al., "Aligned Nanotubes", Chemphyschem 2003, 4, pp. 1150-1169.

Wei, Chen et al., "Multifunctional Chemical Vapor Sensors of Aligned Carbon Nanotube and Polymer Composites", J. Am. Chem. Soc. 2006, 128, No. 5, pp. 1412-1413.

* cited by examiner

POLYMER-CARBON NANOTUBE COMPOSITE FOR USE AS A SENSOR

CROSS REFERENCE TO RELATED APPLICATIONS

This application claims the benefit of U.S. Provisional Application No. 60/716,112 entitled POLYMER-CARBON NANOTUBE COMPOSITES FOR USE IN SENSING APPLICATIONS filed Sep. 12, 2005. The entire contents of said application are hereby incorporated by reference.

BACKGROUND OF THE INVENTION

The present invention relates to a composite film formed by coating aligned carbon nanotubes with a polymer, and to a sensor which incorporates the polymer-carbon nanotube composite film.

Chemical vapor sensors are widely used in applications such as defense, homeland security, health care, and environmental monitoring applications. For example, chemical vapor sensors may be used for real-time sensing of chemical warfare stimulants in a battlefield by monitoring resistivity changes of soldiers' clothing. In recent years, there has been an increasing need for chemical vapor sensors which are efficient, mechanically robust, environmentally stable, and which operate with low power consumption.

Chemical vapor sensors are known which are based on conjugated conducting polymers. Such polymers exhibit the optoelectronic properties of inorganic semiconductors or metals. However, the poor environmental stability associated with most conjugated polymers has precluded their use in practical applications.

Carbon nanotubes have been shown to possess similar optoelectronic properties to that of conjugated polymers. Unlike conjugated polymers, carbon nanotubes are environmentally stable due to their seamless arrangement of hexagon rings without a dangling bond. In addition, their high surface area and small size make carbon nanotubes an attractive candidate for use in chemical vapor sensors. The use of non-aligned carbon nanotubes has been used for detecting gaseous materials, where the detection of gases is achieved by measuring the change in electrical properties of the carbon nanotubes induced by the charge transfer with the gas molecules (e.g., $O_2$, $H_2$, $CO_2$) or by the capacitor change due to physical adsorption of the gas molecules. However, the number of analytes which can be detected using such a carbon nanotube-based sensor is hampered by the limited specific interactions and transduction mechanisms employed.

Accordingly, there is still a need in the art for a chemical vapor sensor which exhibits environmental stability, which exhibits good optoelectronic properties, and which can easily detect a wide variety of analytes.

SUMMARY OF THE INVENTION

The present invention meets that need by providing a polymer-carbon nanotube composite film which may be used as a sensor for detecting, for example, chemical vapors. The sensor incorporating the polymer-nanotube composite exhibits high sensitivity, good selectivity, excellent environmental stability, and has a low power consumption. The sensor may also be adapted for use in sensing mechanical deformation, temperature changes, optical signals, and any other changes that may induce a conductivity change in the composite film.

According to one aspect of the present invention, a composite film for use as a sensor is provided comprising aligned carbon nanotubes which are partially coated along their length with a polymer, i.e., not fully coated. Preferably, the carbon nanotubes are aligned perpendicularly. The aligned carbon nanotubes are preferably prepared by pyrolysis of iron (II) phthalocyanine.

Preferably, the polymer in the composite is selected from poly(vinyl acetate), poly(isoprene), and blends thereof. The polymer is preferably coated onto the carbon nanotubes at a concentration of from about 0.001 to about 100 wt %. The polymer may be applied as a solution comprising the polymer and a suitable solvent. Alternatively, the polymer may be applied as a melt coating.

The resulting composite film may be used as a chemical vapor sensor for use in detecting a broad class of chemical vapors including, but not limited to, acetone, chloroform, cyclohexane, N—N-dimethylformide, ethanol, ethyl acetate, hexane, methanol, tetrachlorocarbon, tetrahydrofuran, and toluene. The sensor is preferably formed by attaching at least two electrodes to the polymer-nanotube composite film. Preferably, wires are connected from the electrodes to a dc resistance meter for measuring resistance changes in response to chemical vapor exposure.

The sensor of the present invention may also be used as a mechanical deformation sensor, an optical sensor, or a temperature sensor. The sensor may be used in any sensing applications where the sensor is capable of detecting a change in conductivity.

Accordingly, it is a feature of the present invention to provide a polymer-carbon nanotube composite for use as a sensor. Other features and advantages of the invention will be apparent from the following description and the accompanying drawings.

DETAILED DESCRIPTION OF THE PREFERRED EMBODIMENTS

We have found that composite films formed from perpendicularly-aligned carbon nanotubes partially coated with an appropriate polymer along their tube length provide the basis for a sensor for detecting a wide variety of chemical vapors. While neither carbon nanotubes nor polymers alone possess the desired sensing properties, a synergetic effect results from the combined polymer/nanotube composite. This synergetic effect is believed to result from the absorption and desorption of chemical vapors by the polymer matrix, which causes changes in the carbon nanotubes with regard to intertube distance and surface resistance perpendicular to the nanotube length.

Preferred carbon nanotubes for use in the present invention are multiwalled carbon nanotubes having a well-graphitized structure. The carbon nanotubes are preferably formed by pyrolyzing iron (II) phthalocyanine (FePc) in an Ar/$H_2$ atmosphere at about 800-1100° C. This results in the formation of perpendicularly aligned carbon nanotubes due to the dense packing of the catalyst particles formed on the substrate surface during the initial stage of nanotube growth. This perpendicular alignment of the carbon nanotubes provides a welldefined large surface area for a sensor resulting in enhanced sensitivity and also facilitates surface modification of the carbon nanotubes with various transduction materials for broadening the variety of analytes which can be detected by the sensor.

Figure 1:
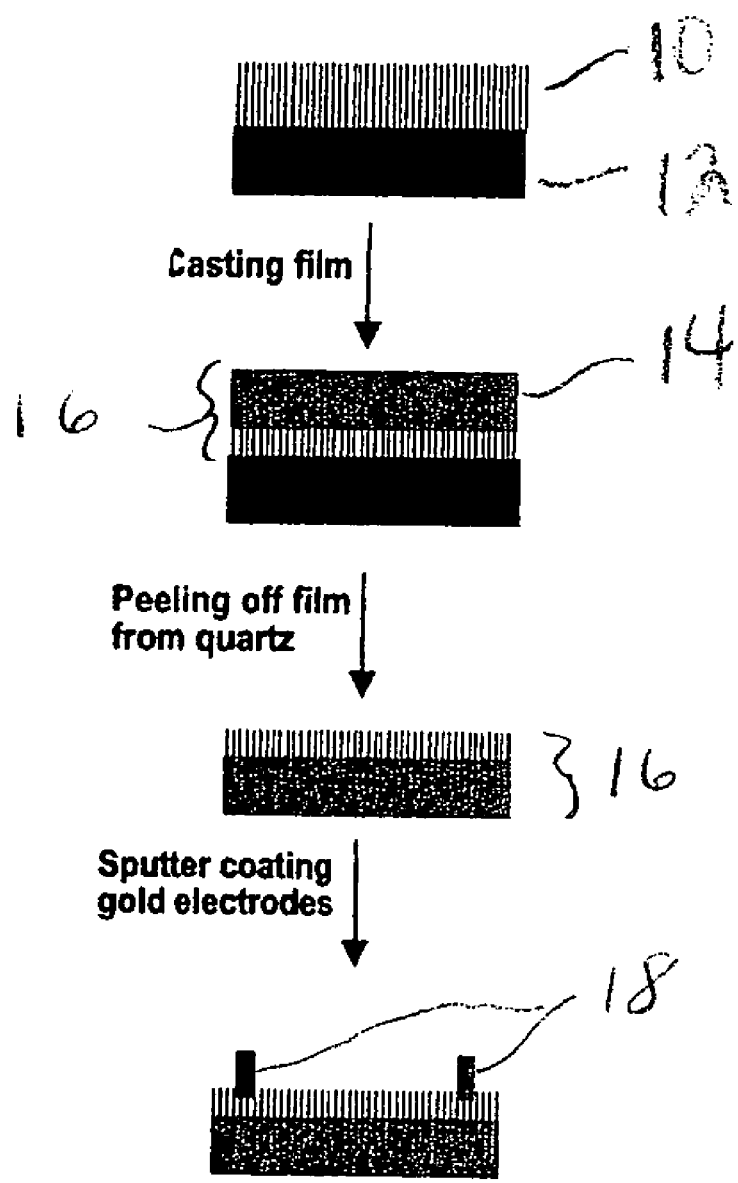
FIG. 1 is a schematic illustration of the method for forming a polymer/carbon nanotube composite in accordance with the present invention.

Referring now to FIG. 1, the method of forming the polymer-carbon nanotube composite film is shown. The aligned carbon nanotubes 10 are preferably formed on a quartz substrate 12. The aligned carbon nanotubes can be transferred to a number of other substrates, including polymer films. The aligned nanotube film can be coated with the polymer solution either before or after transfer occurs.

The polymer solution 14 is preferably drop-coated (i.e., droplets of the polymer solution are placed on the aligned nanotube surface) onto the carbon nanotubes such that the carbon nanotubes are at least partially covered by the polymer along their length. Preferred polymers for use in the present invention include poly(vinyl acetate) and poly(isoprene), or copolymer blends thereof. We have found that the number of analytes which can be detected may be broadened by the use of poly(vinyl acetate) and poly(isoprene) copolymers.

The polymer is preferably applied as a solution comprising a solvent such as toluene at a polymer concentration of between about 0.001 and 100 wt %. It should be appreciated that any suitable organic or inorganic solvent may be used, depending on the nature of the polymer used for coating. Alternatively, the polymer may be applied by melt coating.

After coating, the resulting composite film 16 is preferably air-dried and heated, for example, in an oven. It should be appreciated that the polymer coating thickness may be controlled by regulating the solvent, polymer concentration, the packing density, or the nanotube surface properties through plasma treatment. After heating, the composite film 16 is preferably peeled away from the quartz substrate 12.

Where the composite film is to be used as a chemical vapor sensor, electrodes 18 are preferably deposited on the film, for example, by sputter coating or by lithographic deposition. A dc resistance meter or other measuring device (not shown) may be connected to the electrodes for measuring resistance. The composite film may be used to sense a number of different chemical vapors, including, but not limited to, methanol, hexane, chloroform, tetrahydrofuran (THF), benzene, toluene, and acetone.

In addition to chemical vapor sensors, the polymer/carbon nanotube composite films may also be used for sensing and/or mapping of mechanical deformations as any mechanical deformation normal to the film plane could cause changes in the intertube distance and the surface resistance perpendicular to the nanotube length. Similarly, the same or similar composite films may also be used as temperature sensors, optical sensors, or other sensors.

In order that the invention may be more readily understood, reference is made to the following examples which are intended to illustrate the invention, but not limit the scope thereof.

Example 1

Aligned multiwalled carbon nanotubes having a well-graphitized structure with 50 concentric carbon shells, an outer diameter of 40 nm and a length of 20 μm, were produced on a quartz plate by pyrolyzing iron (II) phthalocyanine (FePc) under $Ar/H_2$ atmosphere at 800-1100° C. The resulting aligned carbon nanotube film was then drop-coated with a polymer coating, with each of the constituent nanotubes being partially covered by the polymer top-down along their length. When necessary, the coating depth for a particular polymer onto the aligned carbon nanotubes was controlled by regulating the nature of solvent, polymer concentration, the packing density, and the nanotube surface properties through plasma treatment.

A solution of polyvinyl acetate (PVAc) or polyisoprene (PI) in toluene at a concentration of 2 wt % was dropped onto the top surface of the aligned multiwall carbon nanotube array to coat about half of the nanotube length. After the composite film was air-dried and baked in an oven at 80° C. overnight, the composite film with aligned carbon nanotubes protruding out from the polymer matrix was then peeled off the quartz substrate and turned upside down as a free-standing film.

Thereafter, the free-standing composite film (5 mm×10 mm×0.2 mm) was put on a non-conducting support (e.g., a glass plate) with the free carbon nanotubes facing up, followed by lithographic deposition of two electrodes (0.1 μm thick). The electrodes were positioned 8 mm apart from each other across the tubes for electrical contacts with gold wires using gold conductive paint. The whole thin film device was then exposed to chemical vapor in a one-neck flask containing chemical solvent and resistance measurements were taken using a dc resistance meter at room temperature.

As a control experiment, an as-synthesized aligned carbon nanotube array on quartz was used to measure dc resistance for all of the chemical vapors investigated in this example (methanol, hexane, chloroform, tetrahydrofuran (THF), benzene, toluene, acetone). As shown, FIG. 2(a) shows no obvious resistance change for the control measurements. In contrast, FIG. 2(b) clearly shows about a 130% increase in resistance for a composite film of PVAc and aligned carbon nanotubes after being exposed to THF vapor for about 2 minutes. Subsequent removal of the THF vapor source caused a loss of about 75% resistance after keeping the PVAc and nanotube composite film in air at room temperature for 2 minutes. It is apparent that the observed resistance changes are due to expansion of the polymer matrix upon exposure to the chemical vapor, which leads to a concomitant increase in the intertube distance. It should be noted that the lost conductivity couldn't be completely compensated in this case due to the inevitable presence of some solvent (THF) in the PVAc matrix. However, after several cycles of the vapor-air exposures with 2-minute intervals, the maximum resistance and the peak height became constant as shown in FIG. 2(b) for greater than 10 minutes, indicating that the solvent absorption/desorption reached an equilibrium state.

The response time, ts, defined as the time required for half of the resistance change, was about 20 seconds, and the time for full recovery, tc, was about 5 minutes for the PVAc and aligned nanotube composite film for sensing THF after reaching the equilibrium state.

Figure 2:
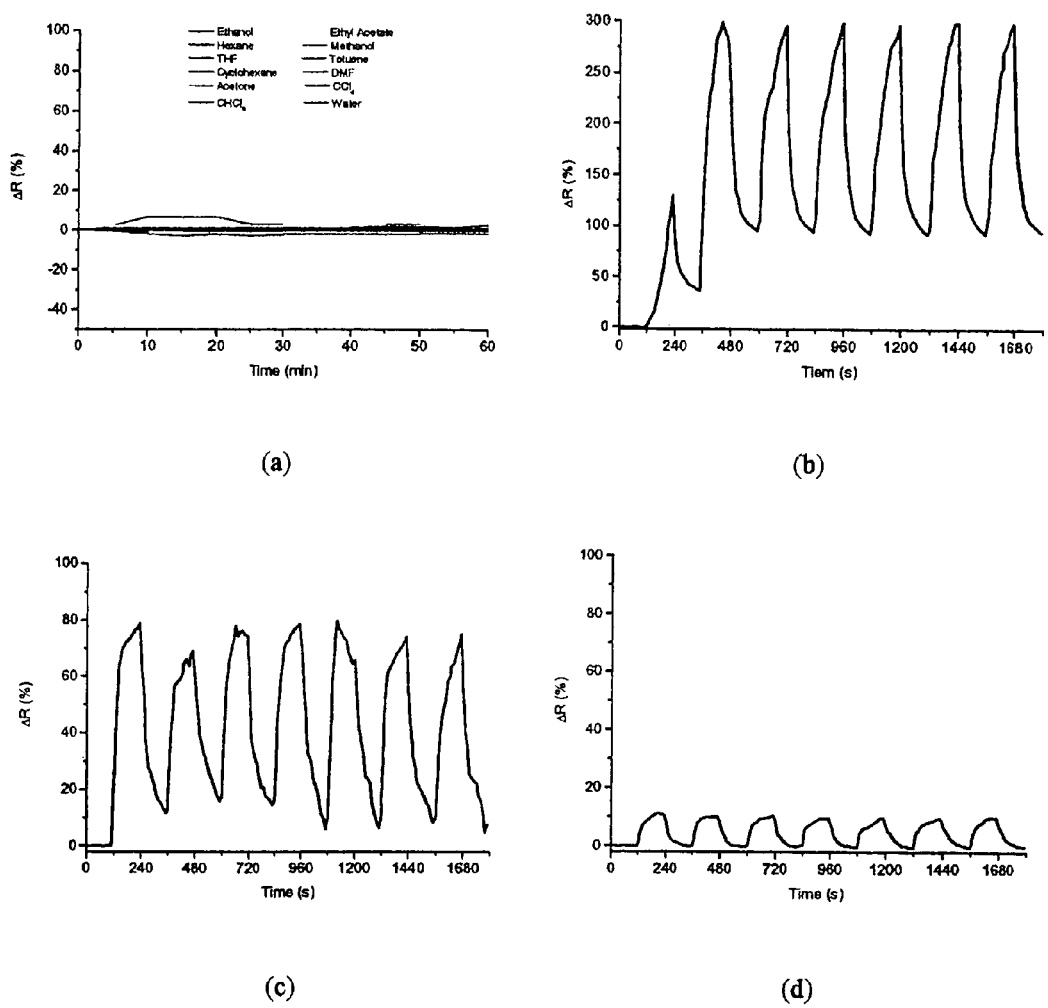
FIGS. 2a-2d are graphs illustrating resistance measurements for various polymer/carbon nanotube composites.

Similar resistance changes were observed for the aligned carbon nanotube and PVAc composite film when exposed to other chemical vapors (e.g. ethanol and cyclohexane; FIGS. 2(c) and (d), respectively). As can be seen in FIG. 2, the equilibrium peak height for THF is about 290% (FIG. 2(b)) with respect to the corresponding value of 75% for ethanol (FIG. 2(c)). This difference can be attributed to the fact that THF is a better solvent than ethanol and can cause a greater expansion of the PVAc matrix, and hence a larger change in resistance. The equilibrium peak height only reached about is 12% upon exposure to a non-solvent (cyclohexane, FIG. 2(d)). However, the conductivity loss by cyclohexane exposure was fully recovered within several minutes after removal of the vapor source.

Figure 3:
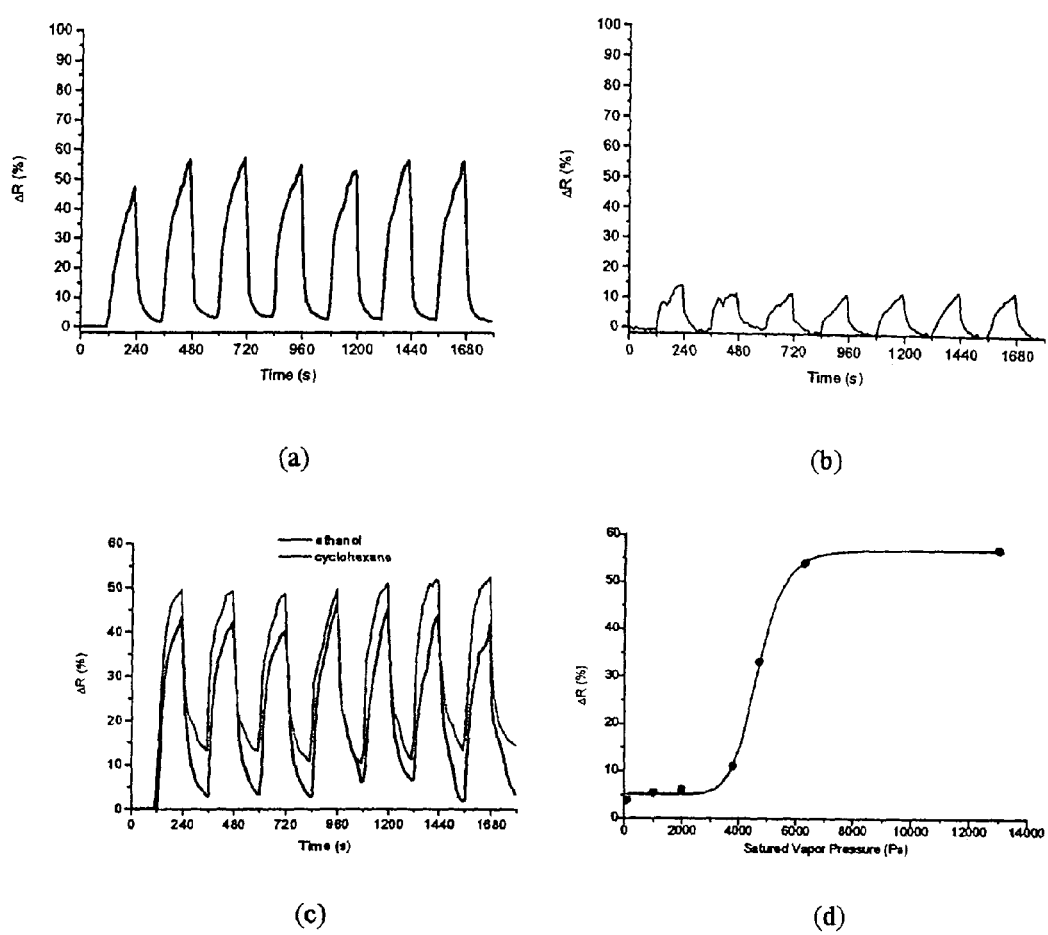
FIGS. 3a-3d are graphs illustrating resistance measurements for various polymer/carbon nanotube composites.

As seen in FIGS. 2(d) and 3(a), the weak response of cyclohexane to the PVAc and aligned carbon nanotube composite film sensor was enhanced by replacing PVAc with PI since cyclohexane is a good solvent for PI. However, because ethanol is a poor solvent to PI, ethanol caused only a weak response with peak height about 10% to the aligned carbon nanotube and PI composite film sensor (FIG. 3(b)).

Example 2

In order to broaden the scope of analytes to be detected by the chemical vapor sensor based on the polymer-nanotube composite films, a solution of PVAc and PI (weight ratio 50:50) in toluene (2 wt %) was used as the coating material to partially cover the aligned nanotubes with the physically blended two-component polymer film.

As seen in FIG. 3(c), the chemical vapor sensors based on the aligned carbon nanotubes and PVAc/PI binary polymer composite show reasonably good responses to both cyclohexane (equilibrium peak height: about 50% vs. 12% for its pure PVAc counterpart) and ethanol (equilibrium peak height about 45% vs. 10% for its pure PI counterpart). Copolymers such as PVAc and PI diblock copolymers could also be used in the composite film.

Table 1 below illustrates that polymer-nanotube composite sensors can be used to detect a wide variety of chemical vapors. The strong dependence of the equilibrium peak height with the partial cyclohexane vapor pressure shown in FIG. 3(d) indicates a high sensitivity and reliability.

TABLE 1

PI/PVAc and aligned carbon nanotube composite film for chemical vapor sensing

| Solvent Vapor | Response time ($t_s$; s) | Peak Height of ΔR (%) | Recovery Time ($t_c$; s) |
|---|---|---|---|
| Acetone | 30 | 63 | 750 |
| Chloroform | 26 | 81 | 570 |
| Cyclohexane | 47 | 48 | 490 |
| N,N-dimethylformide | 15 | 34 | 50 |
| Ethanol | 32 | 45 | 110 |
| Ethyl acetate | 18 | 55 | 170 |
| Hexane | 20 | 53 | 240 |
| Methanol | 16 | 41 | 120 |
| Tetrachlorocarbon | 15 | 71 | 1320 |
| Tetrahydrofuran | 20 | 63 | 280 |
| Toluene | 12 | 25 | 130 |
| Water | N/A | N/A | N/A |

Having described the invention in detail and by reference to preferred embodiments thereof, it will be apparent that modifications and variations are possible without departing from the scope of the invention.

What is claimed is:

1. A method of making a sensor comprising:
   forming aligned carbon nanotubes on the surface of a substrate; wherein said nanotubes are aligned perpendicularly with respect to said substrate;
   partially coating said aligned carbon nanotubes from the top down along their length with a polymer to form a composite film;
   removing said composite film from said substrate; and
   attaching at least two electrodes to said film.

2. The method of claim 1 wherein said polymer is selected from poly(vinyl acetate), poly(isoprene), and blends thereof.

3. The method of claim 1 wherein said polymer is coated onto said carbon nanotubes at a concentration of from about 0.001 to about 100 wt %.

4. The method of claim 1 wherein said aligned carbon nanotubes are formed by pyrolysis of iron (II) phthalocyanine.

5. The method of claim 1 wherein said nanotubes comprises multiwalled carbon nanotubes.

6. The method of claim 1 wherein said polymer coating is applied by drop-coating.

7. The method of claim 1 wherein said polymer coating is applied by melt coating.

* * * * *